United States Patent [19]

Pečar et al.

[11] Patent Number: 5,514,654
[45] Date of Patent: May 7, 1996

[54] N-ACYLDIPEPTIDES, PROCESSES FOR THE PREPARATION THEREOF AND PHARMACEUTICAL COMPOSITIONS CONTAINING THE SAME

[76] Inventors: Slavko Pečar, Veljka Vlahoviča 2/D, YU-61230 Domžale; Marija Sollner, Cesta pod goro 16, YU-61353 Borovnica; Uroš Urleb, Herbersteinova 18; Danijel Kikelj, Trg Oktobrske revolucije 2, both of YU-61000 Ljubljana; Gašper Marc, Pod gradom 6, YU-65271 Vipava; Aleš Krbavčič, Krištofova 8, YU-61000 Ljubljana; Vlado Kotnik, Vlahovičeva 5, YU-61000 Ljubljana; Branka Wraber-Herzog, Zaloška 1, YU-61000 Ljubljana; Saša Simčič, Ob železnici 1, YU-61000 Ljubljana; Alojz Ihan, Spodnji Rudnik T/37, YU-61000 Ljubljana; Lidija Klamfer, Bratovževa ploščad 33, YU-61000 Ljubljana; učka Povšič, Trg Oktobrske revolucije 2, YU-61000 Ljubljana; Zdravko Kopitar, Muljava 7, YU-61234 Mengeš; Anton Štalc, Rašiška 5, Yu-61000 Ljubljana, all of Yugoslavia

[21] Appl. No.: 245,810

[22] Filed: May 18, 1994

Related U.S. Application Data

[63] Continuation of Ser. No. 759,438, Sep. 13, 1991, abandoned.

[30] Foreign Application Priority Data

Sep. 27, 1990 [YU] Yugoslavia ............................. 1830/90

[51] Int. Cl.[6] .......................... A61K 38/00; A61K 38/14; C07K 9/00; C08K 37/00
[52] U.S. Cl. ............................ 514/49; 530/322; 548/209; 548/477; 560/155; 560/169; 562/565; 536/53; 436/826; 436/823
[58] Field of Search .............................. 530/322; 514/19; 436/826, 823; 536/53; 930/DIG. 500; 548/209, 477; 560/155, 169; 562/565

[56] References Cited

PUBLICATIONS

Danklmaier et al., *Liebigs Ann. Chem.*, 145 (1990).
Dollery, et al., The Conduct of Initial Drug Studies in Man, Br. Med. Bull, vol. 26, (1970) pp. 233–235.

Adam, et al., Correlation of Structure and Adjuvant Activity of N-Acetyl Muramyl-L-Alanyl-D-Isoglutamine (MDP), Its Derivatives and Analogues, Anti-Adjuvant and Competition Properties of Stereoisomers, Biochem. Biophys. Res. Commun., vol. 72 (1976), pp. 339–349.

Communications to the Editor, Journal of Medicinal Chem., vol. 24 (1982), pp. 335–337.

Baschang, Muramylpeptides and Lipopeptides: Studies Towards Immunostimulants (1988), pp. 6331–6357.

Honig, et al., Syntheses of Polymeric Vesicles Containing Partial Structures of N-Acetyl-Muramyl-Dipeptide (MDP), Chem. and Phys. of Lipids, vol. 53 (1990), pp. 347–356.

Adam, et al., Muramyl Peptides: Immunomodulators, Sleep Factors, and Vitamins, Medicinal Rev., vol. 4 (1984), pp. 111–152.

*Primary Examiner*—Jill Warden
*Assistant Examiner*—Sheela J. Huff

[57] ABSTRACT

N-acyldipeptides of formula I

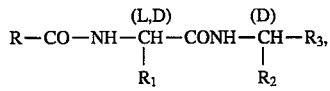

wherein

R represents a rest of formula

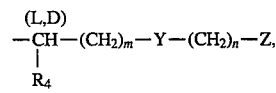

and $R_4$, Y, m, n and Z have the meaning as defined in the description, $R_1$ represents hydrogen, a 1–10 C. alkyl, an optionally substituted methyl or benzyl, $R_2$ represents a —CO—A group, wherein A has the meanings as defined in the description, $R_3$ represents a —$(CH_2)_p$—CO—W group, wherein p and W have the meaning as defined in the description.

10 Claims, No Drawings

N-ACYLDIPEPTIDES, PROCESSES FOR THE PREPARATION THEREOF AND PHARMACEUTICAL COMPOSITIONS CONTAINING THE SAME

This application is a continuation of Ser. No. 07/759,438, filed on Sep. 13, 1991, now abandoned.

TECHNICAL FIELD OF THE INVENTION (IPC C07D)

The invention belongs to the field of pharmaceutical industry and concerns novel N-acyldipeptides, processes for the preparation thereof and pharmaceutical compositions containing the same. The N-acyldipeptides possess immunomodulatory and antitumoral activities.

1. Technical Problem

There exists a continuing need for medicaments having strong immunomodulatory and antitumoral activities, a selective effect upon the immunological system and as few side effects as possible. Recently, peptides having biological activity have been acquiring increasing significance in this field.

2. Prior Art

Muramyl peptides [A. Adam and E. Lederer in Med. Res. Rev. (1984), 4, 111; G. Baschang in Tetrahedron (1989), 22, 6331] are components of microbial cell walls having therapeutically interesting effects upon the immunological system. The synthesis thereof, however, is a very exacting, multi-stage and expensive one [P. Lefrancier and E. Lederer in Fortschr. Chemie Org. Naturstoffe (1981), 40, 1].

N-acetylmuramyl-L-alanyl-D-isoglutamine (muramyl dipeptide, MDP) is the smallest essential structural element of bacterial cell wall having immunomodulatory activity. However, MDP also has several side effects, e.g. a pronounced pyrogenous and somnogenous activity, and its can also cause acute arthritis and anaphylactic reaction.

Japanese authors [Y. Kitaura, H. Takeno, S. Okada, S. Yanischi, K. Hemmi, J. Mori, H. Senah, J. Mine, M. Hashimoto in J. Med. Chem. (1982), 25, 335] have isolated and synthetized various tetrapeptides [lactyl-L-alanyl-D-isoglutamyl-D,L-diaminopimelyl glycine and N-lauroyl-L-alanyl-D-isoglutamyl-L,L-diaminopimelyl glycine] having immunomodulatory properties similar to those of MDP.

Austrian researchers [H. Hönig and R. Zenk in Chem. Phys. Lipids (1990), 53, 347] have described the synthesis of N-(11-metacroylamino-undecanoyl)-L-alanyl-D-isoglutamine and 2-(2-(11-metacroylamino-undecanoyl)aminoethoxy)propanoyl-L-alanyl-D-isoglutamine as a monomer for the polymeric vesicles having the partial MDP structure.

Further, there has been published the synthesis of acyclic MDP analogues [J. Danklmaier and H. Hönig in Liebigs Ann. Chem. (1990), 145], where the authors focused on the synthesis of N-(2-(2-(acylamino)-1-methyl-ethoxy)propanoyl)-L-alanyl-D-isoglutamine compounds having immunomodulatory activity.

Description of the Solution to the Technical Problem with Examples

The invention concerns N-acyldipeptides as well as their analogues and homologues of formula I

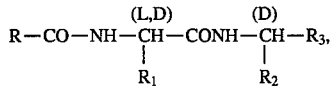

wherein
R represents a rest of formula

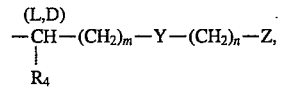

wherein
$R_4$ is hydrogen or 1–8 C alkyl having R or S configuration on the asymmetric centre,
Y is —$CH_2$—, —O—, —COO—, —OCO—, —CONH—, —NHCO—, —NHCONH—, —S—, —SO—, —$SO_2$—, —CS—,
m is 0 or an integer from 1 to 6,
n is 0 or an integer from 1 to 12,
Z is hydrogen, a rest —NH—X—$R_5$, a five-, six- or seven-membered lactam of formula

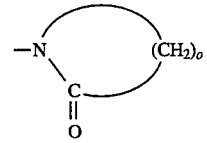

or a cyclic imide of formulae

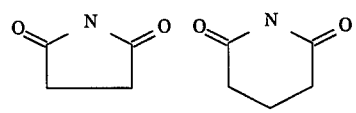

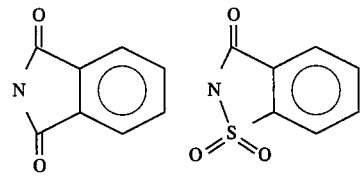

wherein
X is —CO—, —CONH—, —CS—, —CSNH—, —SO—, —$SO_2$— or

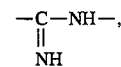

$R_5$ is a straight or branched chain 2–10 C alkyl, an optionally substituted aryl, adamantyl, cyclopentyl, cyclohexyl, cycloheptyl or cyclooctyl,
o is 3, 4 or 5;
$R_1$ represents hydrogen, a straight or branched chain 1–10 C alkyl, hydroxymethyl, halomethyl, alkoxymethyl, aryloxymethyl or benzyl having L or D configuration on the asymmetrical centre,
$R_2$ represents a —CO—A— group,
wherein
A is a —O—$R_6$ or —NH—$R_7$group,
wherein
$R_6$ is hydrogen, a straight or branched chain 1–12 C alkyl or an optionally substituted aryl, and
$R_7$ is hydrogen or a straight or branched chain 1–12 C alkyl;

$R_3$ represents a —$(CH_2)_p$—CO—W group,
wherein
p is 1, 2 or 3,
W is a —O—$R_8$ or —NH—$R_9$ group,
wherein
$R_8$ is hydrogen or a straight or branched chain 1–16 C alkyl, and
$R_9$ is hydrogen, a straight or branched chain 1–20 alkyl, adamantyl, cyclopentyl, cyclohexyl, cycloheptyl or cyclooctyl, having R configuration on the asymmetric centre, the pharmaceutically acceptable salts thereof having immunomodulatory and antitumoral activities and pharmaceutical compositions containing the same. The invention als concerns the processes for the preparation of N-acyldipeptides of formula I, which are considerably shorter, simpler and more economical if compared with known processes for the synthesis of similar peptides and derivatives thereof.

N-acyldipeptides of formula I are prepared by reacting
a) a carboxylic acid of formula II

    II wherein R has the same meaning as in formula I, with a dipeptide or an analogue thereof of formula III

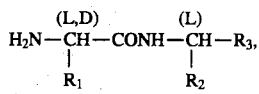    III wherein $R_1$, $R_2$ and $R_3$ have the same meaning as in formula I, or
b) an acid chloride of formula IV

    IV wherein R has the same meaning as in formula I, with a dipeptide or an analogue thereof of formula III

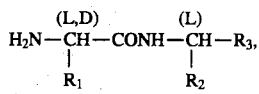    III wherein $R_1$, $R_2$ and $R_3$ have the same meaning as in formula I, or
c) a carboxylic acid of formula II

    II wherein R has the same meaning as in formula I, with an amino acid of formula V

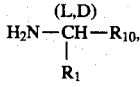    V wherein
$R_1$ has the same meaning as in formula I,
$R_{10}$ is a —COO—$R_{11}$ or —COO$^-$ $B^+$ group,
wherein
$R_{11}$ is hydrogen, 1–6 C alkyl or benzyl, and
$B^+$ is an alkali or earth alkali metal cation or a quaternary ammonium group,
to a compound of formula VI

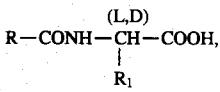    VI wherein R and $R_1$ have the same meaning as in formula I,
which is subsequently reacted with an amino acid of formula VII

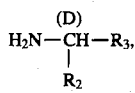    VII wherein $R_2$ and $R_3$ have the same meaning as in formula I, to a compound of formula I, or
d) an acid chloride of formula IV

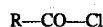    IV wherein R has the same meaning as in formula I, with an amino acid of formula V

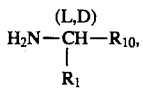    V wherein $R_1$ has the same meaning as in formula I and $R_{10}$ has the above-stated meaning,
to a compound of formula VI

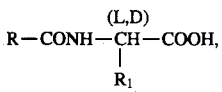    VI wherein R and $R_1$ have the same meaning as in formula I, which is subsequently reacted with an amino acid of formula VII

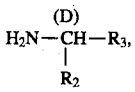    VII wherein $R_2$ and $R_3$ have the same meaning as in formula I, to a compound of formula I,
whereafter in the case that $R_2$ and $R_3$ in formula III and in formula VII represent a —COO—$CH_2$—$C_6H_5$ or a —$(CH_2)_n$—COO—$CH_2$—$C_6H_5$ group respectively and $R_{10}$ in formula V represents a —COO—$C_6H_5$ group, the protective benzyl groups are removed by hydrogenation, and in the case that in formula V $R_{10}$ represents a —COO$R_{11}$ group, wherein $R_{11}$ is a 1–6 C alkyl, the latter is removed by hydrolysis.

The reaction of the carboxylic acid of formula II with dipeptides of formula III, the reaction of the carboxylic acid of formula II with the amino acid of formula V and the reaction of the compound of formula VI with the compound of formula VII are carried out in a polar aprotic solvent such as N,N-dimethylformamide, tetrahydrofuran or 1,4-dioxan, at a temperature from −10° C. to 25° C., using common reagents for the formation of the peptide bond, such as diphenylphosphoryl azide, dicyclohexyl carbodiimide or isobutyl chlorofomate.

The reaction of the acid chloride of formula IV with the amino acid of formula V is carried out in water in the presence of sodium hydroxide, sodium carbonate, sodium hydrogencarbonate or magnesium oxide or in organic solvents such as chloroform, dichloromethane, N,N-dimethylformamide, tetrahydrofuran or 1,4-dioxan, in the presence of an organic base such as triethylamine, pyridine or N-ethylmorpholine, at a temperature from 0° C. to 20° C.

The reaction of the acid chloride of formula IV with the dipeptide or an analogue thereof of formula III is carried out in an organic solvent such as chloroform, dichloromethane, N,N-dimethylformamide, tetrahydrofuran or 1,4-dioxan, in the presence of an organic base such as triethylamine, pyridine or n-ethyl morpholine, at a temperature from 0° C. to 20° C.

The protective benzyl groups in $R_2$, $R_3$ and $R_{11}$ groups are removed by hydrogenation at normal pressure and at room temperature on a Pd/C catalyst. The protective alkyl group $R_{11}$ in the $R_{10}$ groups is removed by hydrolysis in a mixture of dioxan/water or ethanol/water with NaOH or KOH at a temperature from 0° C. to 40° C.

The starting compounds are prepared, unless stated otherwise, according to the methods described in the literature, e.g. the compounds of formula II as described by S. H ünig, E. Lücke and E. Benzing in Chem. Ber (1958), 91, 129; F. P. Prout and J. Cason in J. Org. Chem. (1949), 14, 132; G. Nefkens, G. Tesser and R. Nivard in Recueil (1960), 79, 249; C. R. McArthur, P.M. Worster, J. L. Jiang and C. C. Lenznoff in Can. J. Chem. (1982), 60, 1836; L-alanyl-D-isoglutamine γ-benzyl ester hydrochloride and related dipeptides having D-isoglutamine γ-benzyl ester as the second amino acid are prepared as described by P. Lefrancier and E. Bricas in Bull. Soc. Chim. Biol. (1967), 49, 1257.

BIOLOGICAL TESTS

The following tests were performed:

1. Immunological tests
   1.1 Determination of the number of lymphocytes B and lymphocytes T
   1.2 Determination of the number of macrophages
   1.3 Blast transformation of lymphocytes by mithogens
   1.4 Activation of peritoneal macrophages
   1.5 Determination of haemolytic plaques for the assessment of the maturation of lymphocytes B
2. Antitumour activity
3. Pyrogenous activity
4. Toxicity
1. Immunological tests Immunological studies were performed on female HAN-NmRI strain mice of 3–4 weeks, weighing from 18–21 g.

In tests 1.1 to 1.5, the animals were first administered the Brewer's thioglycolate medium by i.p. injection, which was followed after 6 hours by the injection of 0.5 ml of a solution containing 25 μg, 2.5 μg and 0.25 μg respectively of N-acetyl-muramyl-L-alanyl-D-isoglutamine (muramyl dipeptide, MDP) or of N-(7-oxooctanoyl)-L-alanyl-D-isoglutamine (compound 1, Example 19). Equal doses were administered to the animals on days 2 and 3. On day 4 the animals were sacrificed and the spleen and the peritoneal macrophages were isolated.

1.1 Determination of the number of lymphocytes B and lymphocytes T

To the isolated splenic lymphocytes there were added fluorescein isothiocyanate labelled antimouse antibodies (for the determination of lymphocytes B) and anti-Thy 1 monoclonal antibodies (for the determination of lymphocytes T) respectively. After incubation and rinsing with RPMI 1640 medium (Gibco, Great Britain), the lymphocytes were counted by fluorescence microscopy.

Neither the number of splenic lymphocites B nor of lymphocytes T was altered to a statistically significant extent either by muramyl dipeptide or by compound 1.

1.2 Determination of the number of macrophages

The number of macrophages in the peritoneal cavity washings was determined three days after the stimulation with Brewer's thioglycolate medium. The cells were suspended in ice-cold RPMI 1640 medium, to which trypan blue was added, and counted in Neubauer's chamber.

The number of peritoneal macrophages was not altered to a statistically significant extent either by muramyl dipeptide or by compound 1.

1.3 Blast transformation of lymphocytes by mithogens

Isolated splenic lymphocytes were prepared in a concentration of $1\times10^6$/ml in the RPMI 1640 medium, to which there were added 10% of foetal calf serum (FCS) (Sera-Lab, Great Britain), 1 ml of 200 mM L-glutamine solution and 1 ml of an antibiotic solution (100 U/ml of penicillin and 100 μg/ml of streptomycin) for 100 ml of complete medium. To each flat bottom well of a microtitration plate (T grade, Nunc, Denmark) 100 μl of the cell suspension were distributed. The cells were stimulated in vitro by adding concanavalin A (con A) (Pharmacia, Sweden) at respective concentrations of 16, 8, and 4 μg/ml. Control lymphocyte cultures were grown in basal medium only. The cells were then incubated at 37° C., 5% $CO_2$ and 95% humidity for 2 days, followed by the addition of tritium labelled thymidine. After 16 hours the samples were prepared for the measurement in a β-counter. The results were expressed as incorporation indexes with respect to the control group of the animals.

Studies of concanavalin A influence on the blast transformation ability showed that muramyl dipeptide did not affect the blastic activity of lymphocytes T, whereas the compound 1 in the dose of 25 μg increased this activity statistically significantly for about 70% ($p < 0.05$).

TABLE 1

In vivo immunomodulatory effect of muramyl dipeptide (MDP) and of compound 1 on the blast transformation ability of lymphocytes, stimulated in vitro with concanavalin A

| Substance | Daily dose (μg)* | Amount of active thymidine incorporated in lymphocyte DNA (cpm) $\bar{x} \pm$ s.e.m (n) | p |
|---|---|---|---|
| MDP | 25 | 7460 ± 1980 (5) | >0.05 |
|  | 2.5 | 12440 ± 3540 (5) | >0.05 |
|  | 0.25 | 19840 ± 9400 (5) | >0.05 |
| Compound 1 | 25 | 16380 ± 2950 (5) | <0.05 |
|  | 2.5 | 19080 ± 5470 (5) | >0.05 |
|  | 0.25 | 16860 ± 5210 (5) | >0.05 |
| Control |  | 10130 ± 476 (5) | — |

*Said doses were administered to the animals for 3 consecutive days.

When compared with MDP, compound 1 showed a statistically greater ($p < 0.05$) immunomodulatory effect in lymphocytes T at the dose of 25 μg.

1.4 Activation of peritoneal macrophages

The peritoneal cavity of the animals was rinsed with 4 ml of ice-cold RPMI 1640 medium. The cytolysis of erythrocytes was effected with 0.2% NaCl. The remaining cells were washed twice in a cooled centrifuge at 4° C. and 1500 rpm for 5 minutes with ice-cold RPMI 1640 medium. The cells were re-suspended and the concentration was adjusted to $1.5\times10^6$/ml. The cell suspension was distributed among the flat bottom wells of a microtitration plate (T grade, Nunc, Denmark). After incubating for 2 hours at 37° C., 5% $CO_2$ and 95% humidity, the wells were rinsed with warm RPMI 1640 medium and the adhering macrophages were used for testing.

The macrophages were covered with 100 μl of a 160 μM ferricytochrome C solution in HBSS (Hank's Balanced Salt Solution) without phenol red or with 100 μl of ferricytochrome C in a 200 nM phorbol miristate acetate (PMA, Sigma, St. Louis, USA) solution or with 100 μl of ferricytochrome C, PMA and 340 units/ml of superoxide dismutase (SOD, Sigma, St. Louis, USA), which specifically inhibits the reduction of cytochrome C with the superoxide ion (blank) respectively. After incubating for 90 minutes at 37°

C., 5% $CO_2$ and 95% humidity, the absorbance was measured at the wavelength of 570 nm.

The results are shown in Table 2 as the difference in the absorbance of the test sample and of the blank, calculated for 1 mg of cell protein.

In the studies of macrophage activation it was shown that muramyl dipeptide increased the activity at all three doses by about 120% ($p < 0.01$), whereas the compound 1 at the dose of 0.25 μg did not increase the activity, whereas at the dose of 2.5 and 25 μg the activity was increased by 40% ($p < 0.05$) and 90% ($p < 0.001$) respetively. For the compound 1 the effects were dose-dependent.

As shown in Table 3, after additional macrophage activation with PMA, the activity was increased in both cases at all three doses. In the case of muramyl dipeptide the activity was most increased at the lowest dose, i.e. by about 160% ($p < 0.01$), whereas at both other doses the activity was only increased by about 115% ($p < 0.001$). With compound 1 the activity increased with increasing doses. At the dose of 0.25 μg the effect was increased by about 50% ($p > 0.05$), at the dose of 2.5 μg by about 60% ($p < 0.05$) and at the dose of 25 μg by about 120% ($p < 0.001$) respectively.

In either test at the doses of 2.5 and 25 μg there was no statistically significant difference ($p > 0.05$) between the respective macrophage activation achieved by muramyl dipeptide and by compound 1.

TABLE 2

In vivo immunomodulatory effect of muramyl dipeptide (MDP) and of compound 1 upon macrophage activation without additional in vitro stimulation with phorbol miristate acetate (PMA)

| Substance | Daily dose (μg)* | Difference in absorbancies of the test sample and of the blank per mg of cell protein $\bar{x} \pm$ s.e.m (n) | p |
|---|---|---|---|
| MDP | 25 | 578 ± 81(5) | <0.01 |
|  | 2.5 | 578 ± 42(5) | <0.001 |
|  | 0.25 | 614 ± 35(5) | <0.001 |
| Compound 1 | 25 | 518 ± 20(5) | <0.05 |
|  | 2.5 | 387 ± 56(5) | <0.05 |
|  | 0.25 | 273 ± 40(5) | >0.05 |
| Control |  | 275 ± 26(5) | — |

TABLE 3

In vivo immunomodulatory effect of muramyl dipeptide (MDP) and of compound 1 upon macrophage activation with additional in vitro stimulation with phorbol miristate acetate (PMA)

| Substance | Daily dose (μg)* | Difference in absorbancies of the test sample and of the blank per mg of cell protein $\bar{x} \pm$ s.e.m (n) | p |
|---|---|---|---|
| MDP | 25 | 2138 ± 165 (5) | <0.001 |
|  | 2.5 | 2207 ± 213 (5) | <0.001 |
|  | 0.25 | 2657 ± 595 (5) | <0.05 |
| Compound 1 | 25 | 2200 ± 177 (5) | <0.001 |
|  | 2.5 | 1630 ± 297 (5) | <0.05 |
|  | 0.25 | 1480 ± 336 (5) | >0.05 |
| Control |  | 1004 ± 38 (5) | — |

*Said doses were administered to the animals for 3 consecutive days.

1.5 Determination of haemolytic plaques for the assessment of the maturation of lymphocytes B A 1% suspension of sheep erythrocytes (Institute of Microbiology, Faculty of Medicine, Ljubljana, Yugoslavia) in physiological saline was used for the immunisation. First, individual mice were administered 0.2 ml of this suspension by i.p. injection, followed next day by 0.1 ml (1 μg/mouse) of the test substance. The immunisation was completed on the fifth day after the administration of sheep erythrocytes and the mice were sacrificed.

Their spleens were removed and homogenized in Parker 199 Medium with added amminoacids, streptomycin and sodium carbonate (Torlak, Beograd, Yugoslavia). The lymphocytes were separated on the Ficol Separating Medium (Pharmacia, Uppsala, Sweden). After repeated rinsing with Parker 199 Medium, the cells were resuspended in RPMI 1640 nutrient medium with added 10% of fetal calf serum and streptomycin. To 50 μl of the cell suspension, 450 μl of trypan blue were added and the cells were counted in Neubauer's chamber. The number of lymphocytes per ml of the cell suspension was calculated. To 100 μl of the diluted cell suspension there were added 200 μl of RPMI 1640 nutrient medium, 50 μl of a 10% suspension of sheep erythrocytes and 50 μl of guinea pig complement (Institute of Microbiology, Faculty of Medicine, Ljubljana, Yugoslavia). The reaction mixture (RM) was put into the prepared chambers on the slide, the chambers were sealed with white wax and incubated at 37° C. for 60 minutes. After the completion of the incubation, the plaques were counted under microscope.

The number of plaques per $1 \times 10^6$ cells was calculated according to the following equations:

$$\text{Number of plaques} = \frac{1 \times 10^6 \text{ cells} \times \text{number of plaques per chamber}}{A \text{ cells per chamber}}$$

$$\frac{A \text{ cells}}{\text{per chamber}} = \frac{\text{amount of } RM \text{ per chamber (μl)} \times \text{number of cells in } RM}{\text{amount of } RM \text{ (μl)}}$$

At a dose of 1 μg/mouse, the compound 1 caused a significant increase ($p < 0.05$) of the number of plaques from 86±12.7 (n= 8) to 170±39.9 (n= 8) and to 245±75.5 (n= 7) respectively. The values were reported as $\bar{x}$±s.e.m (n= number of samples).

2. Antitumour activity

The studies were performed on A/J strain mice (Institute Rudjer Bošković, Zagreb, Yugoslavia) of 8 to 10 weeks. All animals used in the same experiment were of the same sex and age.

Fibrosarcoma SA-1 was used as the experimental tumour model. Tumorous cells were obtained from the ascitic form of the SA-1 tumour of the syngeneic A/J mouse. They were implanted into animals dorsilaterally by s.c. injection of $5 \times 10^5$ live tumour cells. The testing was started after the tumours had grown to a volume of 35 mm³. The test substance was injected i.p. on five consecutive days in a dose of 2.5 or 25 μg. The growth of the tumours was monitored by measuring the diameters and the thickness of the tumours. The tumour volumes were calculated according to the formula 0.523×a×b×c (a, b and c being the tumour diameters).

The delay in the growth of each individual tumour was obtained by deducting the relevant time of growth of the tumour in the control group from the time needed for the growth of the tumour to reach the volume of 150 mm³.

In comparison to the control, the antitumour activity of the compound 1 was moderate and statistically significant at the dose of 2.5 μg ($p < 0.002$) and at the dose of 25 μg ($p < 0.05$). However, there was no statistically significant difference in activity between the higher and the lower dose.

TABLE 4

Time needed for the tumour growth to the volume of 150 mm³ and the delay in tumour growth

| Substance | n | Number of days (± SD) | Growth delay (± SD) | p(compared with control) |
|---|---|---|---|---|
| Control Compound 1 | 22 | 5.5 ± 0.8 | | |
| 2.5 µg* | 10 | 7.3 ± 1.5 | 1.8 ± 0.5 | <0.01 |
| 25.0 µg | 11 | 7.0 ± 1.7 | 1.5 ± 0.5 | <0.05 | n = number of experiments
*daily dose; the animals received 5 doses

3. Pyrogenous activity

The pyrogenous activity was determined according to the method of USP XXII.

In contrast to MDP, compound 1 did not show any pyrogenous activity.

4. Toxicity

The average lethal dose ($LD_{50}$) at i.v. application of the compound 1 in male mice was > 250 mg/kg.

All above-described immunological effects of the compound 1 appeared already at a dose which was at least 2000 times lower than $LD_{50}$.

Evaluation of compound 1

Compound 1 is an immunomodulator, which enhances the maturation of lymphocytes B to plasma cells and increases the activity of lymphocytes T as well as that of macrophages but does not alter the number of these immunologically competent cells. In the tested range the effect is dose-dependent. As an immunomodulator it also shows an antitumour activity. In contrast to muramyl dipeptide, which similarly acts upon different immunologically competent cells, compound 1 is neither pyrogenous nor very toxic.

Pharmaceutical preparations

The pharmaceutical preparations of the invention can be in the form of coated pills, tablets, capsules, ampoules or aerosols to be used on mucous membranes. Preparations suitable for parenteral application can also comprise liposomes.

The pharmaceutical preparations of the invention comprise the pharmacologically active compound alone or together with a pharmaceutically acceptable carrier chosen with respect to the mode of application. Pharmaceutical preparations are manufactured according to methods known per se.

The dose, the frequency and the mode of application will depend on various factors such as the intended use (e.g. for the treatment of the primary or secondary immunodeficiency or of various types of infections or for increasing the antitumour activity).

A suitable dose for an adult will be from 0.1 to 250 mg/day. The exact dose, the frequency and the mode of application will be chosen with respect to the activity and pharmacokinetic properties of the particular compound and to other factors that can affect the effect of the drug, such as the type and severity of the condition, the patient's age, weight, sex and response to the medication.

| Injections containing 1 ml each | |
|---|---|
| Compound 1 | 0.1 mg |
| Sodium chloride | 9.0 mg |
| Sodium hydroxide | q.s. |
| Water for injections | 1 ml |

The invention is illustrated by the following non-limiting Examples.

Starting compounds

EXAMPLE 1

N-(2-(2-hydroxyethoxy)-ethyl)-4-chloro-benzamide

To a solution of sodium hydroxide (2.2 g, 0.055 moles) in distilled water (100 ml), aminoethoxyethanol (5.25 g, 0.05 moles) was added and the solution was cooled to 0° C. on an ice bath. Under stirring on the ice bath, p-chloro-benzoylchloride (8.75 g, 0.5 moles) was added thereto drop by drop. The stirring was continued for 3 hours at room temperature and the separated precipitate was filtered off by suction. The mother liquid was extracted with chloroform (3×100 ml). The organic phase was separated, dried with sodium sulfate, filtered and evaporated on a rotary evaporator. The precipitated N-O-di-((4-chloro)-benzoyl)-aminoethoxyethanol was dissolved in dioxan (50 ml) and sodium hydroxide (22 ml of a 1N solution) was added thereto. The solution was stirred for 2 hours at 40° C., water (50 ml) was added thereto and it was extracted with ethyl acetate (5×50 ml). The organic phase was separated, dried with sodium sulfate, filtered and evaporated on a rotary evaporator. The obtained product was crystallized from diethyl ether.

Yield: 9.4 g (77.1%)

Melting point: 83°–84° C.

$^1$H-NMR (CDCl$_3$): δ=2.57 (s, 1H,—OH), 3.48–3,90 (m, 8H, —NHCH$_2$CH$_2$OCH$_2$CH$_2$OH), 6.93 (s (broad), 1H, —NH—), 7.38 (d, 2H, aromatic, H$_2$, H$_6$,), 7.79 (d, 2H, aromatic, H$_3$, H$_5$,).

J=9 Hz

IR (KBr, cm$^{-1}$): 3350, 2980, 2900, 1645, 1600, 1550, 1125, 900, 835, 760

| Analysis for C$_{11}$H$_{14}$ClNO$_3$ | | | |
|---|---|---|---|
| | % C | % H | % N |
| calc.: | 54.22 | 5.79 | 5.75 |
| found: | 54.33 | 5.98 | 5.59 |

EXAMPLE 2

N-(2-(2-hydroxyethoxy)-ethyl)-benzamide

To a solution of sodium hydroxide (2.2 g, 0.055 moles) in distilled water (100 ml), aminoethoxyethanol (5.25 g, 0.05 moles) was added and then, under stirring, benzoyl chloride (7.03 g, 0.05 moles) was added drop by drop at such a rate that the temperature did not exceed 35° C. The stirring was continued for 2 hours at room temperature and the reaction mixture was extracted with chloroform (5×100 ml). The organic phase was separated, dried with sodium sulfate, filtered and evaporated on a rotary evaporator. The product was purified by column chromatography (mobile phase chloroform/methanol 9:1). The product was a viscous liquid.

Yield: 7.8 g (74.6%)

¹H-NMR (CDCl₃): δ=3.58–3.64 (m, 8H, NHCH₂CH₂OCH₂CH₂OH), 7.33–7.84 (m, 5H, phenyl).

IR (NaCl film, cm⁻¹): 3340, 2950, 2890, 1650, 1550, 1500, 1320, 1130, 1080, 720

EXAMPLE 3

N-(2-(2-hydroxyethoxy)-ethyl)-phthalimide

Carbethoxyphthalimide (5.20 g, 0.024 moles) was dissolved in anhydrous tetrahydrofuran (30 ml), the solution was cooled on an ice bath to 0°–5° C. and aminoethoxyethanol (2.37 g, 0.023 moles) in tetrahydrofuran (20 ml) was added drop by drop under stirring. The stirring was continued for 15 minutes on the ice bath and subsequently for 24 hours at room temperature. The solvent was evaporated on a rotary evaporator and the compound was purified by gel chromatography on Sephadex (mobile phase chloroform/methanol 1:1) and crystallization from ethyl acetate.

Yield: 4.32 g (79.8%)

Melting point: 63°–64° C.

¹H-NMR (CDCl₃): δ=3.40–4.00 (m, 8H, —NCH₂CH₂OCH₂CH₂OH), 7.40–7.80 (m, 4H, phthaloyl).

Molecular weight: calculated: 235.24 found: 235

IR (KBr, cm⁻¹): 3560, 2900, 1720, 1480, 1440, 1405, 1370, 1200, 1120, 1090, 1030, 930, 890, 805, 730

| Elemental analysis for $C_{12}H_{13}NO_4$: | | | |
|---|---|---|---|
| | % C | % H | % N |
| calc.: | 61.27 | 5.57 | 5.95 |
| found: | 61.39 | 5.76 | 6.01 |

EXAMPLE 4

2-(2-benzamidoethoxy)-acetic acid

N-(2-(2-hydroxyethoxy)-ethyl)-benzamide (3.14 g, 0.015 moles) was dissolved in acetone (80 ml) and the solution was cooled to 0° C. A solution of chromium(VI) oxide (3.75 g, 0.0375 moles) in sulfuric acid (35%, 78.5 ml) was added drop by drop under stirring at the temperature of 0°–5° C. The stirring was continued at room temperature for 2.5 hours, whereafter the reaction mixture was poured into water (350 ml) and extracted with ethyl acetate (4×100 ml). The organic phase was separated, dried with sodium sulphate, filtered and evaporated on a rotary evaporator. The product was purified by crystallisation from acetone.

Yield: 2.5 g (74.7%)

Melting point: 128°–130° C.

¹H-NMR (DMSO-d₆): δ=3.18 (s, 2H, —OCH₂COOH), 3.70–3.79 (m, 4H, —NHCH₂CH₂O—), 7.44–7.99 (m, 6H, phenyl, —NH—), 8.01 (s, 1H, —COOH).

IR (KBr, cm⁻¹): 3320, 2885, 1720, 1625, 1550, 1220, 1150, 875, 715

| Elemental analysis for $C_{11}H_{13}NO_4$: | | | |
|---|---|---|---|
| | % C | % H | % N |
| calc.: | 59.14 | 5.87 | 6.27 |
| found: | 59.48 | 6.24 | 6.28 |

EXAMPLE 5

2-(2-(4-chlorobenzamide)-ethoxy)-acetic acid

The title compound was prepared from N-(2-(2-hydroxyethoxy)-ethyl)-4-chlorobenzamide in a manner analogous to the one described in Example 4.

Yield: 1.5 g (71.0%)

Melting point: 127°–130° C.

¹H-NMR (DMSO-d₆): δ= 3,13–3,73 (m, 4H, —NHCH₂CH₂O—), 4,06 (s, 2H, —OCH₂COOH), 7,55 (d, 2H, aromatic, H₂, H₆,), 7,90 (d, 2H, aromatic, H₃, H₅,).

J=9 Hz

IR (KBr, cm⁻¹): 3350, 2910, 1730, 1630, 1570, 1200, 1145, 1015, 850, 755

| Elemental analysis for $C_{11}H_{12}ClNO_4$: | | | |
|---|---|---|---|
| | % C | % H | % N |
| calc.: | 51.27 | 4.69 | 5.44 |
| found: | 51.37 | 4.78 | 5.38 |

EXAMPLE 6

2-(2-phthalimidoethoxy)-acetic acid

The title compound was prepared from N-(2-(2-hydroxyethoxy)-ethyl)-phthalimide in a manner analogous to the one described in Example 4.

Yield: 1.0 g (80.2%)

Melting point: 127°–129° C.

¹H-NMR (DMSO-d₆): δ= 3.69–3.77 (m, 4H, —NCH₂CH₂O—), 3.99 (s, 2H, —OCH₂COOH), 7.85 (s, 4H, phthaloyl).

Molecular weight: calculated: 249.23 found: 249

IR (KBr, cm⁻¹): 3220, 1765, 1695, 1400, 1190, 1130, 1045, 1000, 730

| Elemental analysis for $C_{12}H_{11}NO_5$: | | | |
|---|---|---|---|
| | % C | % H | % N |
| calc.: | 57.83 | 4.45 | 5.62 |
| found: | 57.80 | 4.51 | 5.66 |

EXAMPLE 7

N-(2-(2-hydroxyethoxy)ethyl)-1-adamantanecarboxamide

The title compound was prepared from aminoethoxyethanol in a manner analogous to the one described in Example 1.

Yield: 82%

Melting point: 72°–73° C.

¹H-NMR(CDCl₃): δ= 1.71–2.1 (3m, 15H, adamantyl), 2.58 (broad s, 1H, OH), 3.42–3.50 (m, 2H, —NHCH₂—), 3.54–3.62 (m, 4H, 2CH₂), 3.74 (t, 2H, CH₂, J=4.6 Hz), 6.15 (s, 1H, NH).

IR(KBr, cm$^{-1}$): 3346, 2903, 1633, 1531, 1452, 1285, 1133, 1070, 889.

| Elemental analysis for $C_{15}H_{25}NO_3$ | | | |
|---|---|---|---|
| | % C | % H | % N |
| calc.: | 67.38 | 9.42 | 5.24 |
| found: | 67.17 | 9.55 | 5.07 |

EXAMPLE 8

N-(2-(2-hydroxyethoxy)-ethyl)-p-toluenesulphonamide

The title compound was prepared from aminoethoxyethanol in a manner analogous to the one described in Example 1.

Yield: 50%

Melting point: 35°–38° C.

$^1$H-NMR(CDCl$_3$): δ= 2.42 (s, 3H, CH$_3$), 3.12 (t, 2H, J=5.3 Hz, —NH—CH$_2$—), 3.48–3.51 (m, 4H, 2CH$_2$), 3.66–3.69 (m, 2H, CH$_2$), 5.97 (s, 1H, NH), 7.2–7.4 (m, 5H, phenyl).

IR(KBr, cm$^{-1}$): 3400, 2910, 2800, 1325, 1160, 1100, 1070.

EXAMPLE 9

2-(2-(1-adamantanecarboxamido)-ethoxy)-acetic acid

The title compound was prepared from N-(2-(2-hydroxyethoxy)ethyl)-1-adamantanecarboxamide in a manner analogous to the one described in Example 4.

Yield: 86%

Melting point: 120°–124° C.

$^1$H-NMR(CDCl$_3$): δ= 1.62–2.14 (m, 15H, adamantyl), 3.4–3.53 (m, 2H, —NH—CH$_2$—), 3.65 (t, 2H, J=4.7 Hz, —CH$_2$CH$_2$—O), 4.14 (s, 2H, CH$_2$), 6.36 and 6.71 (2t, 1H, —CO—NH—CH$_2$—), 7,93 (broad s, 1H, —COOH).

IR(KBr, cm$^{-1}$): 3374, 2906, 2535, 1728, 1607, 1545, 1453, 1219, 1142, 969, 881, 667.

| Elemental analysis for $C_{15}H_{21}NO_4$ | | | |
|---|---|---|---|
| | % C | % H | % N |
| calc.: | 64.50 | 7.58 | 5.01 |
| found: | 64.12 | 8.01 | 5.40 |

EXAMPLE 10

2-(2-(p-toluenesulphonamido)-ethoxy-acetic acid

The title compound was prepared as an oil from N-(2-(2-hydroxyethoxy)-ethyl)-p-toluene-sulphonamide in a manner analogous to the one described in Example 4.

Yield: 63%

$^1$H-NMR (CDCl$_3$): δ= 2.37 (s, 3H, CH$_3$), 2.88 (td, 2H, —NH—CH$_2$—), 3.42 (t, 2H, J=6 Hz, —CH$_2$—O—), 3.92 (s, 2H, —CH$_2$COOH), 7.30–7.41 and 7.5–7.7 (m, 4H, phenyl), 12.57 (s, 1H, COOH).

IR(KBr, cm$^{-1}$): 3360, 3260, 2910, 2880, 1730, 1320, 1160, 1100.

Compounds according to the invention

EXAMPLE 11

N-(7-oxododecanoyl)-L-alanine methyl ester 7-oxododecanoic acid (1000 mg, 4.67 mmoles) and L-alanine methyl ester hydrochloride (656 mg, 4.7 mmoles) were dissolved in N,N-dimethylformamide (5 ml). The solution was cooled to 0° C. and diphenylphosphoryl azide (1300 mg, 4.72 mmoles) and triethylamine (950 mg, 0.95 mmoles) were added thereto. The reaction mixture was stirred for 1 hour on an ice bath and for 24 hours at room temperature. The resulting suspension was diluted with ethyl acetate (30 ml) and washed successively with citric acid (0.52M; 3×5 ml), water (3×5 ml), saturated NaCl solution (3×5 ml), saturated NaHCO$_3$ solution (3×5 ml), water (3×5 ml) and saturated NaCl solution (3×5 ml). The organic phase was dried with MgSO$_4$ and filtered, the filtrate was evaporated and the compound was precipitated from n-hexane/diethyl ether.

Yield: 64%

Melting point: 66°–70° C.

Melting point determined by the DSC method: $T_{max}$= 69.9° C.

Molecular weight: calculated: 299.41 found: 299

| Elemental analysis for $C_{16}H_{29}NO_4 \cdot H_2O$ | | | |
|---|---|---|---|
| | % C | % H | % N |
| calc.: | 60.54 | 9.84 | 4.41 |
| found: | 60.15 | 9.42 | 4.36 |

IR (KBr, cm$^{-1}$): 3340, 2980–2960, 2860, 1760, 1715, 1670–1650, 1350, 1460, 1390, 1290, 1180

EXAMPLE 12

N-(7-oxotetradecanoyl)-L-alanine methyl ester

The title compound was prepared from 7-oxotetradecanoic acid in a manner analogous to the one described in Example 11.

Yield: 83%

Melting point: 61°–64° C.

Molecular weight: calculated: 327.47 found: 327

| Elemental analysis for $C_{18}H_{33}O_4$ | | | |
|---|---|---|---|
| | % C | % H | % N |
| calc.: | 66.02 | 10.15 | 4.27 |
| found: | 65.88 | 10.36 | 4.21 |

IR (KBr, cm$^{-1}$): 3320, 2920–2910, 2850, 1730, 1690, 1630, 1530, 1440, 1370, 1220, 1170

EXAMPLE 13

N-(7-oxodecanoyl)-L-alanine methyl ester

The title compound was prepared from 7-oxodecanoic acid in a manner analogous to the one described in Example 11.

Yield: 63%

Melting point: 51°–54° C.

Molecular weight: calculated: 271.36 found: 271

| Elemental analysis for $C_{14}H_{25}NO_4$ | | | |
|---|---|---|---|
| | % C | % H | % N |
| calc.: | 61.99 | 9.22 | 5.16 |
| found: | 61.68 | 9.63 | 5.46 |

IR (KBr, cm$^{-1}$): 3300, 2920–2900, 2840, 1730, 1690, 1630–1320, 1530, 1440, 1370, 1220, 1150

EXAMPLE 14

N-(7-oxododecanoyl)-L-alanine

N-(7-oxododecanoyl)-L-alanine methyl ester (700 mg, 2.34 mmoles) was dissolved in dioxane (10 ml) and a solution of NaOH (1M; 4 ml) was slowly added thereto under stirring. After 20 minutes the reaction mixture was evaporated, the residue was diluted with water (25 ml) and cooled on an ice bath to 0° C. The cooled solution was acidified with 1M HCl to pH 2. The precipitate that separated was filtered off by suction (thus there were obtained 305 g of the product) and the filtrate was extracted with ethyl acetate (3×10 ml). A total of 630 mg of the product was obtained, with was crystallized from diethyl ether/methanol.

Yield: 94%

Melting point: 79°–80° C.

Molecular weight: calculated: 285.11 found: 285

| Elemental analysis for $C_{15}H_{27}NO_4$ | | | |
|---|---|---|---|
| | % C | % H | % N |
| calc.: | 63.13 | 9.53 | 4.90 |
| found: | 63.33 | 9.84 | 4.90 |

IR (KBr, cm$^{-1}$): 3380–3360, 2980–2940, 2880, 1730–1700, 1650, 1550–1520, 1420, 1390, 1250

EXAMPLE 15

N-(7-oxotetradecanoyl)-L-alanine

The title compound was prepared from N-(7-oxotetradecanoyl)-L-alanine methyl ester in a manner analogous to the one described in Example 14.

Yield: 92%

Melting point: 84°–86° C.

Molecular weight: calculated: 313.44 found: 313

| Elemental analysis for $C_{17}H_{31}NO_4$ | | | |
|---|---|---|---|
| | % C | % H | % N |
| calc.: | 65.14 | 9.97 | 4.47 |
| found: | 65.39 | 10.09 | 4.22 |

IR (KBr, cm$^{-1}$): 3380–3360, 2980–2940, 2880, 1730–1700, 1670–1660, 1540–1520, 1470, 1420, 1390.

EXAMPLE 16

N-(7-oxododecanoyl)-L-alanyl-D-isoglutamine benzyl ester

N-(7-oxododecanoyl)-L-alanine (590 mg, 2.07 mmoles) and D-isoglutamine benzyl ester hydrochloride (565 mg, 2.07 mmoles) were dissolved in N,N-dimethylformamide (7 ml). The solution was cooled to 0° C. and diphenylphosphoryl azide (578 mg, 2.1 mmoles) and triethylamine (424 mg, 4.2 mmoles) were added thereto. The reaction mixture was stirred for 1 hour on an ice bath and for another 48 hours at room temperature. To the resulting suspension there were added benzene (5 ml) and ethyl acetate (25 ml) and it was washed successively with citric acid (0.52M; 3×5 ml), water (3×5 ml), saturated NaCl solution (3×5 ml), saturated NaHCO$_3$ solution (3×5 ml), water (3×5 ml) and saturated NaCl solution (3×5 ml). The organic phase was dried with MgSO$_4$ and filtered, the filtrate was evaporated and the compound was precipitated from n-hexane/diethyl ether.

Yield: 86%

Melting point: 159°–161° C.

Melting point determined by the DSC-method: 161° C.

Molecular weight: calculated: 503.64 found: 446 (M-C$_4$H$_9$)

| Elemental analysis for $C_{27}H_{41}N_3O_6$ | | | |
|---|---|---|---|
| | % C | % H | % N |
| calc.: | 64.39 | 8.20 | 8.34 |
| found: | 64.28 | 8.42 | 8.30 |

IR (KBr, cm$^{-1}$): 3460–3440, 3300, 3220, 3080, 2980–2940, 2880, 1740, 1680, 1650–1610, 1560–1540, 1450, 1380, 1260, 1190.

EXAMPLE 17

N-(7-oxotetradecanoyl)-L-alanyl-D-isoglutamine benzyl ester

The title compound was prepared from N-(7-oxotetradecanoyl)-L-alanine in a manner analogous to the one described in Example 16.

Yield: 88%

Melting point: 137°–141° C.

Molecular weight: calculated: 531.69 found: 531

| Elemental analysis for $C_{29}H_{45}N_3O_6$ | | | |
|---|---|---|---|
| | % C | % H | % N |
| calc.: | 65.51 | 8.53 | 7.90 |
| found: | 65.10 | 8.05 | 7.30 |

IR (KBr, cm$^{-1}$): 3420, 3320–3280, 3200, 3080, 2960–2940, 2860, 1720, 1680, 1650–1620, 1560–1530, 1450, 1390, 1290, 1190.

EXAMPLE 18

N-(7-oxooctanoyl)-L-alanyl-D-isoglutamine benzyl ester

The title compound was prepared from N-(7-oxooctanoyl)-L-alanine in a manner analogous to the one described in Example 16.

Yield: 55%

Melting point: 162° C.

Melting point determined by the DSC-method: T$_{max}$= 162.2° C.

Molecular weight: calculated: 447.53 found: 339 (M-Bz)

Elemental analysis for $C_{23}H_{33}N_3O_6$

|  | % C | % H | % N |
|---|---|---|---|
| calc.: | 61.73 | 7.43 | 9.39 |
| found: | 62.06 | 7.48 | 9.00 |

IR (KBr, cm$^{-1}$): 3420, 3320, 3280, 3080, 2940, 2880, 1750, 1715, 1680, 1660, 1640–1610, 1550, 1460, 1430, 1390, 1270.

EXAMPLE 19

N-(7-oxooctanoyl)-L-alanyl-D-isoglutamine (compound No. 1)

N-(7-oxooctanoyl)-L-alanyl-D-isoglutamine benzyl ester (310 mg, 0.69 mmoles) was dissolved in methanol (20 ml) and Pd/C (10%; 130 mg) was added thereto. Hydrogen was passed in for 30 minutes, it was filtered and the filtrate was evaporated. The compound was crystallized from diethyl ether/ethanol.

Yield: 81%

Melting point: 169°–171° C.

Melting point determined by the DSC-method: $T_{max}$= 172.4° C.

Molecular weight: calculated: 357.4 found: 357

Elemental analysis for $C_{16}H_{27}N_3O_6$

|  | % C | % H | % N |
|---|---|---|---|
| calc.: | 53.77 | 7.61 | 11.75 |
| found: | 53.42 | 7.75 | 11.42 |

IR (KBr, cm$^{-1}$): 3420, 3320, 3280, 2960, 2880, 1680, 1660, 1650–1630, 1430.

$^1$H-NMR (300 MHz, DMSO-d$_6$): δ= 1.14–1.26 (m, 2H, CH$_2$CH$_2$CH$_2$), 1.15–1.21 (d, 3H, J=7.0 Hz, CHCH$_3$), 1.38–1.56 (m, 4H, J=7.38 Hz, CH$_2$CH$_2$CH$_2$CH$_2$CH$_2$), 1.62–1.76 and 1.92–2.02 (m, 1H each, CH$_2$-β-iGln), 2.06 (s, 3H, CH$_3$CO), 2.04–2.12 (t, 2H, J=7.33 Hz, CH$_3$COCH$_2$CH$_2$), 2.14–2.24, (t, 2H, J=7.63 Hz, CH$_2$COOH), 2.36–2.44 (t, 2H, J=7.33 Hz, CH$_2$CONH), 4.09–4.23 (m, 2H, CH-iGln, CH-Ala), 7.09–7.2 and 7.45–7.75 (2s, 1H each, CONH$_2$), 8.05–8.15 (2d, 1H each, NH).

EXAMPLE 20

N-(7-oxododecanoyl)-L-alanyl-D-isoglutamine

N-(7-oxododecanoyl)-L-alanyl-D-isoglutamine benzyl ester (780 mg, 1.55 mmoles) was suspended in absolute methanol (20 ml) and Pd/C (10%; 100 mg) was added thereto and hydrogen was passed in at normal pressure for 1 hour. The reaction mixture was filtered by suction, the catalyst was removed and the filtrate was evaporated. The solid product was precipitated from methanol/anhydrous diethyl ether.

Yield: 76.5%

Melting point: 148°–151° C.

Molecular weight: calculated: 413.14 found: 414 (M+ 1)

Elemental analysis for $C_{20}H_{35}N_3O_6$

|  | % C | % H | % N |
|---|---|---|---|
| calc.: | 58.09 | 8.53 | 10.16 |
| found: | 57.87 | 8.23 | 9.46 |

IR (KBr, cm$^{-1}$): 3420, 3300, 3220, 2980–2940, 2880, 1740–1700, 1680, 1650–1630, 1610, 1560–1530, 1460, 1430, 1390, 1250.

EXAMPLE 21

N-(5-phthalimidopentanoyl)-L-alanyl-D-isoglutamine benzyl ester

L-alanyl-D-isoglutamine benzyl ester hydrochloride (548 mg, 1.6 mmoles) and 5-phthalimidopentanoic acid (400 mg, 1.6 mmoles) were dissolved in N,N-dimethylformamide (8 ml). The solution was cooled to 0° C. and diphenylphosphoryl azide (495 mg, 1.8 mmoles) and triethylamine (323 mg, 3.2 mmoles) were added thereto. The reaction mixture was stirred for 1 hour at 0° C. and for 24 hours at room temperature. The reaction mixture was diluted by ethyl acetate (40 ml) and the organic phase was washed successively with citric acid (0.52M; 3×10 ml), water (3×10 ml), saturated NaCl solution (3×10 ml), saturated NaHCO$_3$ solution (3×10 ml), water (3×10 ml) and saturated NaCl solution (3×10 ml). The organic phase was dried with MgSO$_4$ and filtered, the filtrate was evaporated and the product was precipitated from n-hexane/diethyl ether. The compound was filtered off and crystallized from acetone.

Yield: 65%

Melting point: 172°–174° C.

Melting point determined by the DSC-method: $T_{max}$= 174.7° C.

Molecular weight: calculated: 536.59; found: 446 (M-Bz)

Elemental analysis for $C_{28}H_{32}N_4O_7$

|  | % C | % H | % N |
|---|---|---|---|
| calc.: | 62.67 | 6.01 | 10.44 |
| found: | 62.74 | 6.28 | 10.48 |

IR (KBr, cm$^{-1}$): 3420, 3300, 3080, 2980–2940, 2880, 1750, 1730–1700, 1680, 1650–1630, 1410, 1190.

EXAMPLE 22

N-(5-phthalimidopentanoyl)-L-alanyl-D-glutamine dibenzyl ester

L-alanyl-D-glutamic acid dibenzyl ester hydrochloride (685 mg, 2 mmoles) and 5-phthalimidopentanoic acid (494 mg, 2 mmoles) were dissolved in N,N-dimethylformamide (8 ml). The solution was cooled to 0° C. and diphenylphosphoryl azide (604 mg, 2.2 mmoles) and triethylamine (404 mg, 4 mmoles) were added thereto. The reaction mixture was stirred for 1 hour at 0° C. and for 48 hours at room temperature. The reaction mixture was diluted by ethyl acetate (50 ml) and successively washed with citric acid (0.52M; 3×10 ml), water (3×10 ml), saturated NaCl solution (3×10 ml), saturated NaHCO$_3$ solution (3×10 ml), water (3×10 ml) and saturated NaCl solution (3×10 ml). The organic phase was dried with MgSO$_4$ and filtered, the filtrate was evaporated and the product was precipitated from diethyl ether. The analytically pure product was obtained after filtration by suction.

Yield: 70%

Melting point: 114°–117° C.

Molecular weight: calculated: 627.7 found: 627

| Elemental analysis for $C_{35}H_{37}N_3O_8$ | | | |
|---|---|---|---|
|  | % C | % H | % N |
| calc.: | 66.97 | 5.94 | 6.69 |
| found: | 66.62 | 6.13 | 6.31 |

IR (KBr, cm$^{-1}$): 3320, 3080, 2980–2940, 1740–1710, 1660–1640, 1560–1540, 1450, 1420, 1350, 1280–1260, 1180–1160.

EXAMPLE 23

N-(5-phthalimidobutanoyl)-L-alanyl-D-glutamine dibenzyl ester

The title compound was prepared from 4-phthalimidobutanoic acid in a manner analogous to the one described in Example 22.

Yield: 65%

Melting point: 88°–90° C.

Molecular weight: calculated: 613.67 found: 613

| Elemental analysis for $C_{34}H_{35}N_3O_8$ | | | |
|---|---|---|---|
|  | % C | % H | % N |
| calc.: | 66.54 | 5.75 | 6.84 |
| found: | 66.83 | 6.04 | 6.44 |

IR (KBr, cm$^{-1}$): 3320, 3080, 2980, 2960, 1750–1720, 1650–1630, 1460, 1390, 1280.

EXAMPLE 24

N-(5-phthalimidopentanoyl)-L-alanyl-D-glutamic acid

To N-(5-phthalimidopentanoyl)-L-alanyl-D-glutamic acid dibenzyl ester (310 mg, 0.49 mmoles) in methanol (30 ml), Pd/C (10%; 140 mg) was added and it was hydrogenated at atmospheric pressure for 3 hours. The reaction mixture was filtered, the filtrate was evaporated and the product was crystallized from diethyl ether/methanol.

Yield: 75%

Melting point: 101°–105° C.

Molecular weight: calculated: 447.45 found: 448

| Elemental analysis for $C_{21}H_{25}N_3O_8$ | | | |
|---|---|---|---|
|  | % C | % H | % N |
| calc.: | 56.37 | 5.63 | 9.38 |
| found: | 56.17 | 5.85 | 9.48 |

IR (KBr, cm$^{-1}$): 3320–3280, 3080, 2960–2940, 1730–1710, 1650, 1560–1530, 1410, 1340

$^1$H-NMR (300 MHz, DMSO-d$_6$): δ= 1.2 (d, 3H, CHCH$_3$), 1.3–1.65 (m, 1H each, CH$_2$-β-Glu), 2.05–2.19 (t, 2H, CH$_2$-γ-Glu), 2.2–2.39 (t, 2H, J=5.61 Hz, CH$_2$CONH), 3.4–3.55 (t, 2H, J=5.43 Hz, CH$_2$NH), 4.1–4.2 (m, 1H, CH-Glu), 4.2–4.35 (m, 1H, CH-Ala), 7.7–7.9 (s, 4H, phthaloyl), 8.12 (s, 2H, NH).

EXAMPLE 25

N-(2-(2-(4-chlorobenzamido)-ethoxy)-acetyl)-L-alanyl-D-isoglutamine benzyl ester The title compound was prepared from 2-(2-(4-chlorobenzamido)-ethoxy)-acetic acid in a manner analogous to the one described in Example 21.

Yield: 67%

Melting point: 141°–143° C.

$^1$H-NMR(DMSO-d$_6$): δ= 1.21 (d, 3H, J=7.0 Hz, CHCH$_3$), 1.69–1.86 and 1.93–2.10 (2m, 1H each, CH$_2$-β-Gln), 2.36 (t, 2H, J= 7.8 Hz, CH$_2$-β-Gln), 3.46 (t, 2H, J=5.1 Hz, NCH$_2$CH$_2$O), 3.61 (t, 2H, NCH$_2$CH$_2$O), 3.93 (s, 2H, —OCH$_2$CO), 4.11–4.25 (m, 1H, CH-Gln), 4.33 (t, 1H, J=7.03 Hz, CH-Ala), 5.08 (s, 2H, CH$_2$Ph), 7.14 and 7.32 (2s, 1H each, CONH$_2$), 7.35 (s, 5H, phenyl), 7.53 (d, 2H, J=8.6 Hz, H$_2$, in H$_6$,), 7.85 (d, 1H, J=8.1 Hz, NH), 7.88 (d, 2H, J=8.6 Hz, H$_3$, in H$_5$,), 8.21 (d, 1H, J=8.1 Hz, NH), 8.70 (t, 1H, J=5.4 Hz, CONHCH$_2$).

IR(KBr, cm$^{-1}$): 3380, 3290, 2940, 1725, 1660, 1540, 1325, 1175, 1090, 1015, 760, 700.

| Elemental analysis for $C_{26}H_{31}N_4O_7$ | | | |
|---|---|---|---|
|  | % C | % H | % N |
| calc.: | 57.09 | 5.71 | 10.24 |
| found: | 57.07 | 5.99 | 10.15 |

EXAMPLE 26

N-(2-(2-phthalimidoethoxy)-acetyl)-L-alanyl-D-isoglutamine benzyl ester

The title compound was prepared from 2-(2-phthalimidoethoxy)-acetic acid in a manner analogous to the one described in Example 21.

Yield: 88%

Melting point: 205°–206° C.

$^1$H-NMR(DMSO-d$_6$): δ=1.19 (d, 3H, J=6.8 Hz, CHCH$_3$), 1.68–1.85 and 1.93–2.10 (2m, 1H each, CH$_2$-β-Gln), 2.35 (t, 2H, J=7.7 Hz, CH$_2$-γ-Gln), 3.68 (t, 2H, J=5.0 Hz, NCH$_2$CH$_2$O), 3.82 (t, 2H, NCH$_2$CH$_2$O), 3.91 (s, 2H, —OCH$_2$CO), 4.10–4.21 (m, 1H, CH-Gln), 4.27 (t, 1H, J=6.10 Hz, CH-Ala), 5.08 (s, 2H, COOCH$_2$Ph), 7.11 and 7.33 (2s, 1H each, CONH$_2$), 7.36 (s, 5H, phenyl), 7.81–7.86 (m, 4H, phthaloyl), 7.69 and 8.16 (2d, 1H each, NH, J=7.6 Hz).

IR(KBr, cm$^{-1}$): 3340, 3380, 3275, 3050, 2945, 1765, 1710, 1660, 1515, 1390, 1270, 1195, 1140, 1030, 1020, 760, 725.

| Elemental analysis for $C_{27}H_{30}N_4O_8$ | | | |
|---|---|---|---|
|  | % C | % H | % N |
| calc.: | 60.22 | 5.61 | 10.40 |
| found: | 60.09 | 5.78 | 10.40 |

EXAMPLE 27

N-(2-(2-phthalimidoethoxy)-acetyl)-L-alanyl-D-glutamine dibenzyl ester

The title compound was prepared from 2-(2-phthalimidoethoxy)-acetic acid in a manner analogous to the one described in Example 22.

Yield: 66%

Melting point: 108°–109° C.

$^1$H-NMR(CDCl$_3$): δ=1.40 (d, 3H, J= 7.1 Hz, CHCH$_3$), 1.68–1.85 and 1.92–2.07 (2m, 1H each, CH$_2$-β-Glu), 2.39 (t, 2H, J=8.1 Hz, CH$_2$-γ-Glu), 3.64–3.77 (m, 2H, J= 5.1 Hz, NCH$_2$CH$_2$O), 3.86–3.97 (m, 4H, NCH$_2$CH$_2$O and OCH$_2$CO), 4.4–4.52 (m, 1H, CH-Glu), 4.53–4.63 (m, 1H, CH-Ala), 5.08 and 5.1 (2s, 2H each, COOCH$_2$Ph), 7.07 and 7.11 (2s, 1H each, NH), 7.27–7.40 (m, 10H, phenyl), 7.66–7.89 (m, 4H, phthaloyl).

IR(KBr, cm$^{-1}$): 3302, 1774, 1745, 1719, 1699, 1649, 1521, 1406, 1270, 1207, 1187, 1115, 1022, 870.

| Elemental analysis for C$_{34}$H$_{35}$N$_3$O$_9$ | | | |
|---|---|---|---|
| | % C | % H | % N |
| calc.: | 64.86 | 5.60 | 6.67 |
| found: | 64.72 | 5.71 | 6.76 |

EXAMPLE 28

N-(2-(2-phthalimidoethoxy)-acetyl)-L-alanyl-D-isoglutamine

N-(2-(2-phthalimidoethoxy)-acetyl)-L-alanyl-D-isoglutamine benzyl ester (0.1 g, 1.9 mmoles) was dissolved in glacial acetic acid (10 ml), Pd/C (10%; 0.015 g) was added thereto and hydrogen was passed in for 6 hours. The reaction mixture was filtered and the filtrate was evaporated.

Yield: 85%

Melting point: 229°–232° C.

$^1$H-NMR(DMSO-d$_6$): δ= 1.20 (d, 3H, J=6.8 Hz, CHCH$_3$), 1.79–1.89 and 1.94–2.02 (2m, 1H each, CH$_2$-β-Gln), 2.19 (t, 2H, J= 7.8 Hz, CH$_2$-γ-Gln), 3.69 (t, 2H, J=5.3 Hz, NCH$_2$CH$_2$O), 3.81 (t, 2H, NCH$_2$CH$_2$O), 3.91 (s, —OCH$_2$CO), 4.03–4.09 (m, 1H, CH-Gln), 4.28 (t, 1H, J= 7.02 Hz, CH-Ala), 7.09 and 7,29 (2s, 1H each, CONH$_2$), 7.68 (d, 1H J= 7.0 Hz, NH), 7.89–7.99 (m, 4H, phthaloyl), 8.14 (d, 1H, NH, J=81 Hz, NH).

IR(KBr, cm$^{-1}$): 3440, 3360, 3274, 2910, 1755, 1665, 1635, 1540, 1390, 1130.

| Elemental analysis for C$_{20}$H$_{24}$N$_4$O$_8$ | | | |
|---|---|---|---|
| | % C | % H | % N |
| calc.: | 53.57 | 5.39 | 12.49 |
| found: | 53.36 | 5.65 | 12.12 |

EXAMPLE 29

N-(2-(2-phthalimidoethoxy)-acetyl)-L-alanyl-D-glutamic acid

The title compound was prepared from N-(2-(2-phthalimidoethoxy)-acetyl)-L-alanyl-D-glutamine dibenzyl ester in a manner analogous to the one described in Example 28.

Yield: 55%

Melting point: 192°–195° C.

$^1$H-NMR(DMSO-d$_6$): δ= 1.20 (d, 3H, J=6.9 Hz, CHCH$_3$), 1.68–1.84 and 1.90–2.06 (2m, 1H each, CH$_2$-β-Glu), 2.41 (t, 2H, J=7.3 Hz, CH$_2$-γ-Glu), 3.69 (t, 2H, J=5.2 Hz, NCH$_2$CH$_2$O), 3.81 (t, 2H, NCH$_2$CH$_2$O), 3.91 (s, 2H, —OCH$_2$CO), 4.14–4.24 (m, 1H, CH-Gln), 4.28–4.41 (m, 1H, CH-Ala), 7.57 (d, 1H, NH), 7.80–7.93 (m, 4H, phthaloyl), 8.24 (d, 1H, NH), 12.4 (broad s, 2H, COOH).

IR(KBr, cm$^{-1}$): 3372, 3311, 2952, 1768, 1747, 1708, 1660, 1636, 1559, 1393, 1205, 1135, 1021, 719.

| Elemental analysis for C$_{20}$H$_{23}$N$_3$O$_9$ | | | |
|---|---|---|---|
| | % C | % H | % N |
| calc.: | 53.45 | 5.16 | 9.35 |
| found: | 53.40 | 5.22 | 9.39 |

EXAMPLE 30

N-(2-(2-(1-adamantanecarboxamido)-ethoxy)-acetyl)-L-alanyl-D-isoglutamine benzyl ester The title compound was prepared from 2-(2-(1-adamantanecarboxamido)-ethoxy)acetic acid in a manner analogous to the one described in Example 21.

The compound was purified by column chromatography on silica gel with acetone as the mobile phase.

Yield: 35%

Melting point: 57°–64° C.

$^1$H-NMR(CDCl$_3$): δ= 139 (d, 3H, J=7.0 Hz, CHCH$_3$), 1.65–2.02 (m, 15H, adamantyl), 1.93–2.02 and 2.17–2.26 (2m, 1H each, CH$_2$-β-Gln), 2.48 (t, 2H, J=7.3 Hz, CH$_2$-γ-Gln), 3.45 (t, 2H, J=5.1 Hz, NCH$_2$CH$_2$O), 3.57 (t, 2H, NCH$_2$CH$_2$O), 3.96 (s, 2H, —OCH$_2$COOH), 4.39–4.50 (m, 1H, CH-Gln), 4.30–4.58 (m, 1H, CH-Ala), 5.11 (s, 2H, COOCH$_2$Ph), 6.23 and 6.32 (2s, 1H each, CONH$_2$), 6.98 (broad s, 1H, NH), 7.25–7.34 (m, 5H, phenyl), 7.73 (d, 1H, J=8.1 Hz, NH).

IR(KBr, cm$^{-1}$): 3405, 2906, 1734, 1654, 1534, 1452, 1385, 1261, 1167, 1116, 978, 910, 752, 698.

EXAMPLE 3

N-(2-(2-(1-adamantanecarboxamido)-ethoxy)-acetyl)-L-alanyl-D-isoglutamine

The title compound was prepared from N-(2-(2-(1-adamantanecarboxamido)-ethoxy)-acetyl)-L-alanyl-D-isoglutamine benzyl ester in a manner analogous to the one described in Example 20.

Yield: 97%

Melting point: 84°–86° C.

$^1$H-NMR(DMSO-d$_6$): δ= 1.25 (d, 3H, J=6.9 Hz, CHCH$_3$), 1.58–2.06 (m, 17H, adamantyl and CH$_2$-β-Gln); 2.20 (t, 2H, J= 7.6 Hz, CH$_2$γ-Gln), 3.24–3.45 (t, 2H, J= 5.2 Hz, NCH$_2$CH$_2$O), 3.46 (t, 2H, NCH$_2$CH$_2$O), 3.88 (s, 2H, —OCH$_2$COOH), 4.10–4.26 (m, 1H, CH-Gln), 4.28–4.40 (m, 1H, CH-Ala), 7.10 (broad s, 1H, NH), 7.47 (t, 1H, J=5.4 Hz, NH), 7.78 (d, 1H, J=7.1 Hz, NH), 8.16 (d, 1H, J=8.4 Hz, NH).

IR(KBr, cm$^{-1}$): 3372, 2906, 1707, 1654, 1533, 1450, 1287, 1255, 1173, 1137, 977, 673, 583.

We claim:

1. N-acyldipeptides having formula I

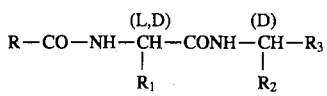

I wherein
R represents

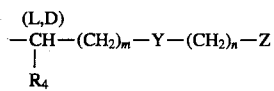

wherein $R_4$ is hydrogen,

Y is —$CH_2$—, —O—, —CO—, —COO—, —OCO—, —CONH—, m is an integer from 1 to 4, n is an integer from 1 to 6, Z is hydrogen, —NH—X—$R_5$,
wherein
X is —CO—
$R_5$ is a straight $C_{2-10}$ alkyl, adamantyl, cyclopentyl, cyclohexyl, cycloheptyl or cyclooctyl, or Z is a cyclic imide of the formulae

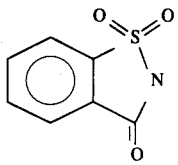

or

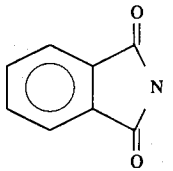

$R_1$ represents hydrogen, a straight or branched chain $C_{2-10}$ alkyl, hydroxymethyl or alkoxymethyl, $R_2$ represents a —CO—A— group,
wherein
A is a —O—$R_6$ or —NH—$R_7$ group,
wherein $R_6$ is hydrogen, a straight or branched chain $C_{1-10}$ alkyl or benzyl, $R_7$ is hydrogen or a straight or branched chain $C_{1-10}$ alkyl, $R_3$ represents a —$(CH_2)_p$—CO—W group,
wherein
p is 2
W is —O—$R_8$ or NH—$R_9$ group,
wherein $R_8$ is hydrogen or a straight or branched $C_{1-10}$ alkyl, $R_9$ is hydrogen, a straight or branched $C_{1-10}$ alkyl, adamantyl, cyclopentyl, cyclohexyl, cyclohexyl, cycloheptyl or cyclooctyl, or the pharmaceutically acceptable salts thereof having immunomodulatory and antitumoral activities.

2. Pharmaceutical compositions containing as the active ingredient a therapeutically effective amount of N-acyldipeptide of formula I of claim 1 together with pharmaceutically acceptable carriers.

3. The N-acyldipeptide of claim 1 being a L-alanyl-D-isoglutamine.

4. The N-acyldipeptide of claim 1 being selected from the group consisting of N-(7-oxooctanoyl)-L-alanyl-D-isoglutamine, N-(5-phthalimidopentanoyl)-L-alanyl-D-isoglutamine, and N-(2-(2-(1-adamantanecarboxamido)-ethoxy)-acetyl)-L-alanyl-D-isoglutamine.

5. The N-acyldipeptide of claim 1 being N-(7-oxooctanoyl)-L-alanyl-D-isoglutamine.

6. The N-acyldipeptide of claim 1 being N-(7-oxododecanoyl)-L-alanyl-D-isoglutamine.

7. The N-acyldipeptide of claim 1 being N-(7-oxotetradecanoyl)-L-alanyl-D-isoglutamine dibenzyl ester.

8. The N-acyldipeptide of claim 1 being N-(5-phthalimidopentanoyl)-L-alanyl-D-isoglutamine dibenzyl ester.

9. The N-acyldipeptide of claim 1 being N-(2-(2-(1-adamantanecarboxamido)-ethoxy)-acetyl)-L-alanyl-D-isoglutamine.

10. The N-acyldipeptide of claim 1 being selected from the group consisting of N-(-7-oxooctanoyl)-L-alanyl-D-isoglutamine, N-(7-oxododecanoyl)-L-alanyl-D-isoglutamine, N-(7-oxotetradecanoyl)-L-alanyl-D-isoglutamine dibenzyl ester, N-(5-phthalimidopentanoyl)-L-alanyl-D-isoglutamine dibenzyl ester and N-(2-(2-(1-adamantanecarboxamido)-ethoxy)-acetyl)-L-alanyl-D-isoglutamine.

* * * * *

UNITED STATES PATENT AND TRADEMARK OFFICE
CERTIFICATE OF CORRECTION

PATENT NO. :   5,514,654
DATED      :   May 7, 1996
INVENTOR(S):   Pecar et al.

It is certified that error appears in the above-identified patent and that said Letters Patent is hereby corrected as shown below:

On the title page, item [73] Assignees: should read

Univerza Edvarda Kardelja v. Ljubljani,
    VDO Fakulteta za narovoslovje in
    tehnologijo, n.sol.o.

LEK, tovarna farmacevtskih in kemcnih
    izdelkov, p.o.

Signed and Sealed this

Twelfth Day of November, 1996

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,514,654
DATED : May 7, 1996
INVENTOR(S): Pecar et al.

It is certified that error appears in the above-identified patent and that said Letters Patent is hereby corrected as shown below:

On title page, item , [76] Inventors: "ucka" should be ---Lucka---.

Column 18, line 52, please change "glutamine" to ---glutamic acid"

Column 19, line 21, please change "glutamine" to ---glutamic acid"

Column 20, last line, please change "glutamine" to ---glutamic acid"

Column 21, line 64, please change "glutamine" to ---glutamic acid"

Column 22, line 45, please change "EXAMPLE 3" to ---EXAMPLE 31---.

Signed and Sealed this

Twelfth Day of August, 1997

Attest:

BRUCE LEHMAN

*Attesting Officer*  *Commissioner of Patents and Trademarks*